(12) United States Patent
van Ockenburg et al.

(10) Patent No.: US 7,261,850 B2
(45) Date of Patent: Aug. 28, 2007

(54) METHODS OF MAKING BALLOON CATHETER TIP

(75) Inventors: Ben van Ockenburg, Ten Boer (NL); Edwin A. Schulting, Haren (NL); Frederik A. Snippe, Groningen (NL)

(73) Assignee: Cordis Corporation, Miami Lakes, FL (US)

( * ) Notice: Subject to any disclaimer, the term of this patent is extended or adjusted under 35 U.S.C. 154(b) by 659 days.

(21) Appl. No.: 10/881,593

(22) Filed: Jun. 30, 2004

(65) Prior Publication Data

US 2006/0004399 A1    Jan. 5, 2006

(51) Int. Cl.
   *B29C 61/02*    (2006.01)
   *B29C 65/18*    (2006.01)

(52) U.S. Cl. .................... 264/230; 264/248; 264/271.1; 264/334

(58) Field of Classification Search ...................... None
See application file for complete search history.

(56) References Cited

U.S. PATENT DOCUMENTS

| | | | |
|---|---|---|---|
| 4,251,305 A * | 2/1981 | Becker et al. ................. 156/86 |
| 4,636,272 A * | 1/1987 | Riggs ........................ 156/158 |
| 4,737,219 A * | 4/1988 | Taller et al. ................. 156/215 |
| 4,913,701 A | 4/1990 | Tower | |
| 5,267,959 A | 12/1993 | Forman | |
| 5,531,700 A * | 7/1996 | Moore et al. .......... 604/164.13 |
| 5,549,580 A | 8/1996 | Diaz | |
| 5,649,909 A * | 7/1997 | Cornelius ................ 604/96.01 |
| 5,769,819 A | 6/1998 | Schwab et al. | |
| 6,048,485 A * | 4/2000 | Field et al. .................. 264/322 |
| 6,402,720 B1 | 6/2002 | Miller et al. | |
| 6,599,462 B1 * | 7/2003 | Miraki ....................... 264/456 |
| 6,702,972 B1 * | 3/2004 | Markle ........................ 264/230 |
| 7,147,817 B1 * | 12/2006 | Lim et al. ................. 264/289.6 |
| 7,172,796 B2 * | 2/2007 | Kinoshita et al. .......... 428/36.3 |

(Continued)

FOREIGN PATENT DOCUMENTS

JP      7-24070      *    1/1995

OTHER PUBLICATIONS

European Search Report EP 05 25 3857 dated Oct. 26, 2005 with Annex to the European Search Report.

*Primary Examiner*—Edmund H. Lee
(74) *Attorney, Agent, or Firm*—Michael W. Montgomery

(57) ABSTRACT

A balloon catheter for medical treatment of a patient has an improved tip design and methods of making the tip. The balloon catheter has a flexible shaft with proximal and distal ends, a hub affixed to the proximal end, and a balloon affixed to the shaft near the distal end. At least a distal portion of the shaft includes a tubular inner body, and the balloon has a distal leg affixed to the inner body. A short, tubular tip member is placed in contact with the distal end of the inner body, and a shrink tube is placed around the point of contact. A wire mandrel is passed through a lumen defined by the inner body and tip member. While the shrink tube is heated, compressing the tip member and inner body, the mandrel is moved. This combination of heat, radial pressure, and mandrel movement causes a blending of the materials of the inner body and the tip member. The resulting joint of the tip member and inner body is both strong and flexible.

7 Claims, 8 Drawing Sheets

U.S. PATENT DOCUMENTS

2003/0032920 A1    2/2003   Wantink
2003/0135231 A1    7/2003   Goodin et al.
2005/0197687 A1    9/2005   Molael et al.

* cited by examiner

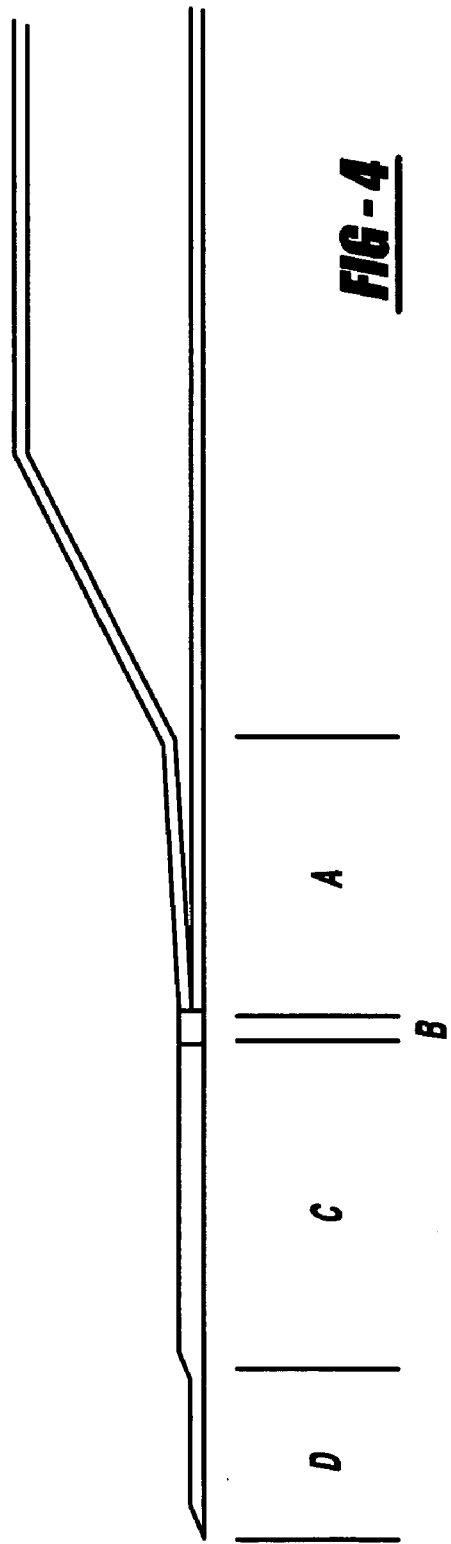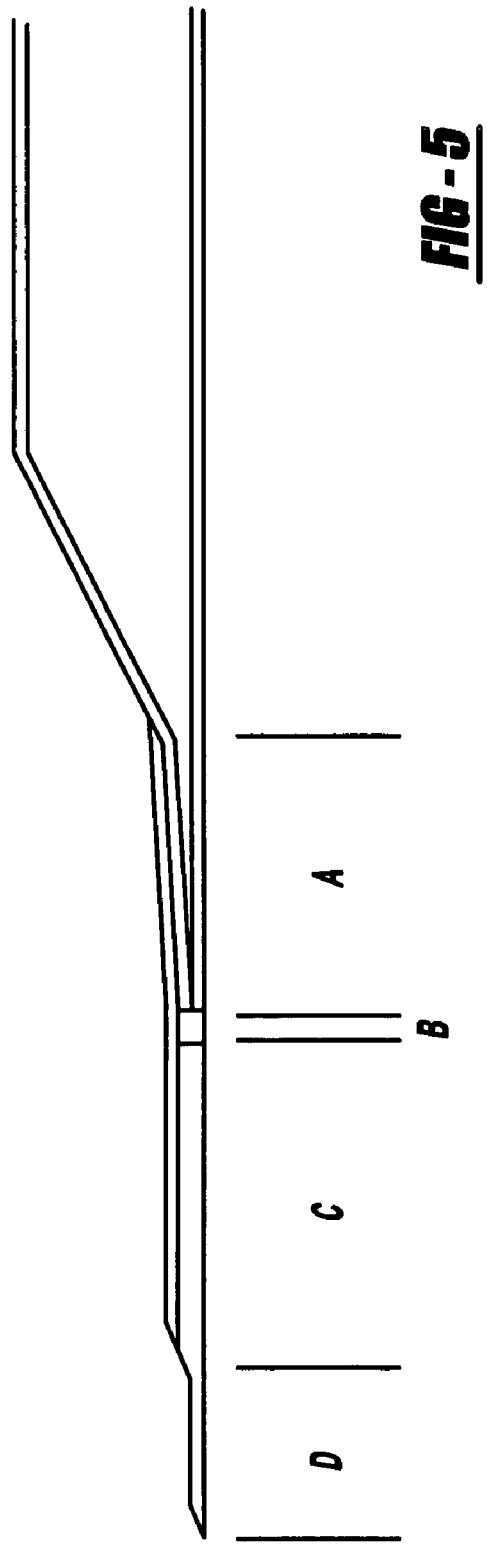

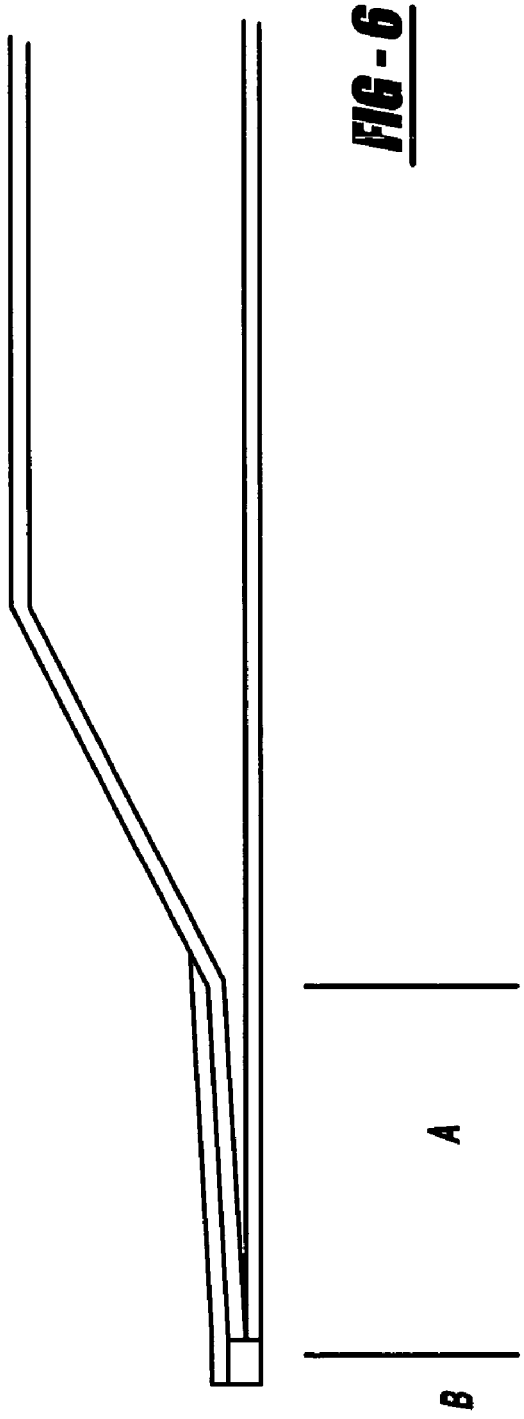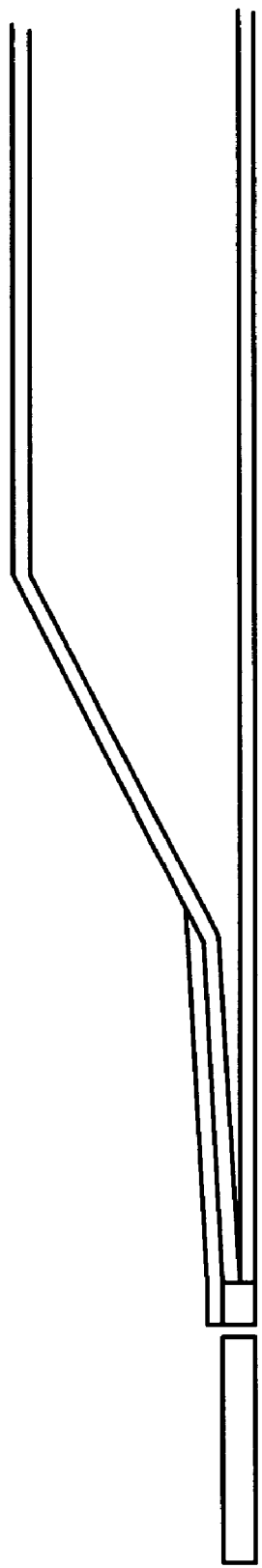

METHODS OF MAKING BALLOON CATHETER TIP

BACKGROUND AND SUMMARY OF THE INVENTION

1. Technical Background

The present invention relates generally to medical devices, and more particularly to balloon catheter tip designs, and methods of making such catheter tips.

2. Discussion

Balloon catheters are used in a variety of therapeutic applications, including many vascular treatments such as angioplasty, and delivery of medical devices such as stents. Angioplasty can be used to treat vascular disease, in which blood vessels may be partially or totally blocked or narrowed by a lesion or stenosis. In many instances of vascular disease, a local area of a blood vessel may become narrowed. This narrowing is called a lesion or stenosis, and may take to form of hard plaque, cholesterol, fats, or viscous thrombus. Such a stenosis may cause heart attack or stroke, which are significant health problems affecting millions of people each year.

During angioplasty, an expansive force may be applied to the lumen of the stenosis, which may be a vessel constriction or narrowing due to plaque buildup or thrombus, etc. This outward pressing of a narrowing at the desired site in a body passage is intended to partially or completely reopen or dilate that body passageway or lumen, increasing its inner diameter or cross-sectional area. The objective of this procedure is to increase the inner diameter or cross-sectional area of the vessel passage or lumen through which blood flows, to encourage greater blood flow through the newly expanded vessel.

After or during angioplasty, a mesh scaffold called a stent may be deployed in the vessel passage. The stent will generally be allowed to remain permanently, tending to hold open the vessel.

The present invention relates to methods of joining polymer tubes and to resulting assemblies of joined polymer tubes. A prior method of joining two polymer tubes is to select two tubes having the same or similar inner and outer dimensions, place their ends together and heat them to form a simple heat-seal or "butt fuse". The tubes may be cylindrical or not, including for example tubes having a cross-section that is square, rectangular, triangular, or any other regular or irregular polygon. Also, the tubes may have the same inner and outer dimensions, or the inner and/or outer dimensions, or the inner and/or outer dimensions may be slightly different, as long as overlapping or abutting surfaces are defined.

A butt seal can be made easily and quickly. However, a butt seal may present a sharp transition in material characteristics, such as lubricity or flexibility. Also, a butt seal may itself be less flexible than is desirable, or may be less strong of a joint than is desirable.

In contrast, the present invention joins polymer tubes such that the joint itself is flexible, and is stronger than other methods. Using the principles of the present invention, at least two polymer tubes are placed in contact. These tubes will be referred to as the "joinder tubes." They may contact each other in an abutting or overlapping arrangement, or a combination of both. A shrink tube is placed around the polymer tubes to be joined (the joinder tubes). The shrink tube tends to radially shrink when heated, and may have a high lubricity and a higher melting temperature than the joinder tubes. A mandrel is inserted within the joinder tubes. The mandrel may be a metal wire or other suitable material thin enough to pass through the lumens of the joinder tubes.

To join the joinder tubes, the shrink tube is heated to cause the joinder tubes to melt slightly, or to a temperature greater than the glass transition temperatures or melting temperatures of the joinder tubes, and the mandrel is moved while the shrink tube imparts inward radial pressure on the joinder tubes. The movement of the mandrel may be along a longitudinal axis in one direction or the opposite direction, or it may be moved back and forth, and/or it may be rotated.

The resulting seal is strong and flexible, with a transition zone of blended material properties, rather than an abrupt transition.

As an example, the present invention will be described in relation to coronary, peripheral, and neurovascular angioplasty and/or stenting. However, it should be understood that the present invention relates to any catheter having polymer tubes joined with a method using the features of the present invention, and is not limited to catheters for a particular therapeutic treatment. Another example of the present invention is any two polymer tubes, for example the main shaft of a catheter, that are joined using a shrink tube, heat, and a moving mandrel.

Some balloon catheters have a relatively long and flexible tubular shaft defining one or more passages or lumens. The shaft extends between a hub at a proximal end to a distal end, and a balloon is located near the catheter distal end. The catheter shaft defines an inflation lumen for conducting inflation fluid from an inflation port defined by the proximal hub to the balloon interior, so a physician can selectively inflate or deflate the balloon.

The shaft may also define a guidewire lumen extending from a distal guidewire port at the distal end of the catheter to a proximal guidewire port located at a position proximal from the balloon. The proximal guidewire port may be defined by the hub, referred to as an "over-the-wire" arrangement, or may be positioned at some intermediate point on the shaft between the hub and balloon, referred to as a "rapid exchange" arrangement. Structurally, the guidewire lumen may be defined by a tubular inner body extending from a distal end of the catheter proximally through the entire length of the balloon catheter. Whatever structural element defines the guidewire lumen, the inner diameter or cross-sectional area of the guidewire lumen is preferably large enough to accommodate the size of the desired guidewire. Likewise, the inner diameter of the guidewire lumen in the region of the balloon may be constant, to facilitate easy movement of the guidewire within the guidewire lumen.

One possible shaft design is a coaxial arrangement of tubular inner and outer bodies. A balloon defines an interior volume and has a proximal leg and a distal leg, with the distal balloon leg being affixed to a distal end of the inner body, and the proximal balloon leg being affixed to a distal end of the outer body.

During a common treatment method for using such a balloon catheter, a physician advances the catheter into the body of the patient, by directing the catheter distal end percutaneously through an incision and along a body passage, until the balloon is located within the desired site. The term "desired site" refers to the location in the patient's body currently selected for treatment by a physician.

As the balloon catheter is advanced along the desired vascular path, the performance of the catheter design may be evaluated by analyzing various characteristics, including flexibility, lubricity, pushability, trackability, crossability, low profile and others. Flexibility may relate to bending stiffness of a medical device (balloon catheter and/or stent, for example) in a particular region or over its entire length, or may relate to the material hardness of the components. Lubricity may refer to reducing friction by using low-friction materials or coatings. Pushability may relate to the column strength of a device or system along a selected path. Trackability may refer to a capability of a device to successfully follow a desired path, for example without prolapse. Crossability may be clarified by understanding that physicians prefer to reach the desired site with the balloon catheter while encountering little or no friction or resistance. Profile may refer to a maximum lateral dimension of the balloon catheter, at any point along its length.

As an example of prior balloon catheters, U.S. Pat. No. 6,402,720 entitled "Balloon Catheter With Elongated Flexible Tip", issued to Miller et al. on Jun. 11, 2002 shows a balloon catheter having a hub, a catheter shaft having an outer and inner tube, a balloon and a flexible tip.

These and various other objects, advantages and features of the invention will become apparent from the following description and claims, when considered in conjunction with the appended drawings.

BRIEF DESCRIPTION OF THE DRAWINGS

FIGS. 4-15 are diagrammatic cross-section views depicting method steps according to the principles of the present invention.

DETAILED DESCRIPTION OF THE PREFERRED EMBODIMENT

Figure 1:
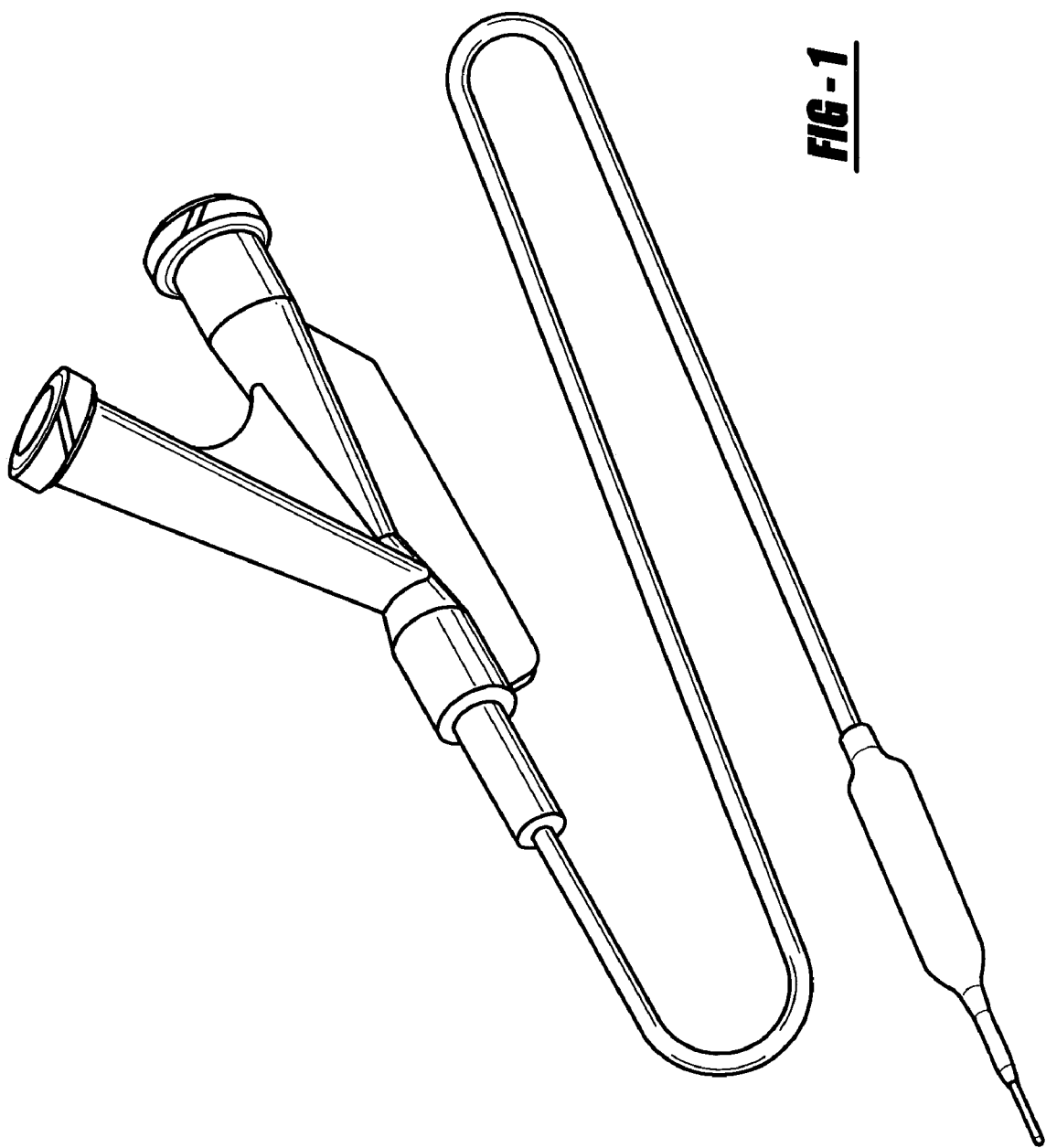
FIG. 1 is a perspective view of a balloon catheter.
Figure 2:
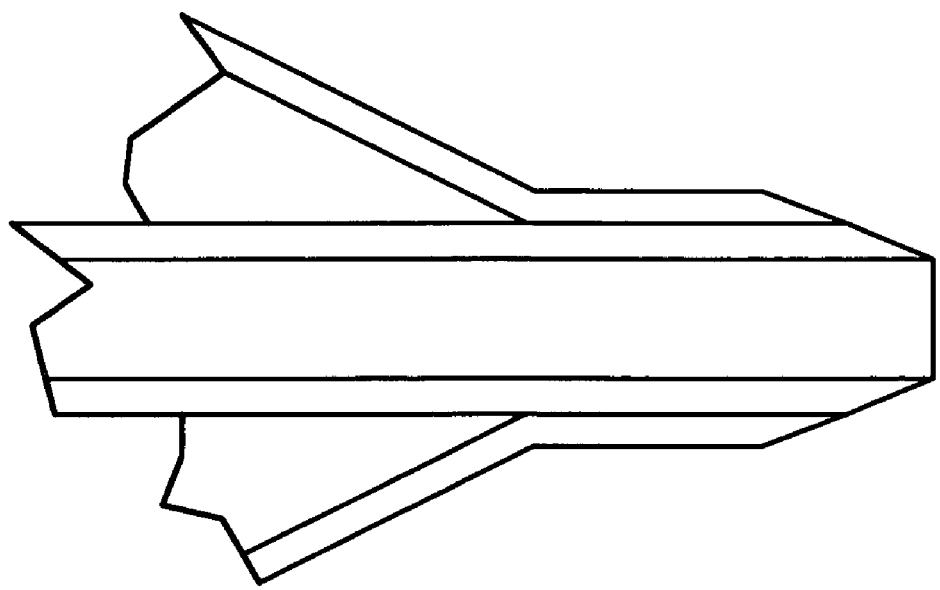
FIGS. 2 and 3 are partial cross-section views of a balloon catheter, in the region of the distal tip.
Figure 3:
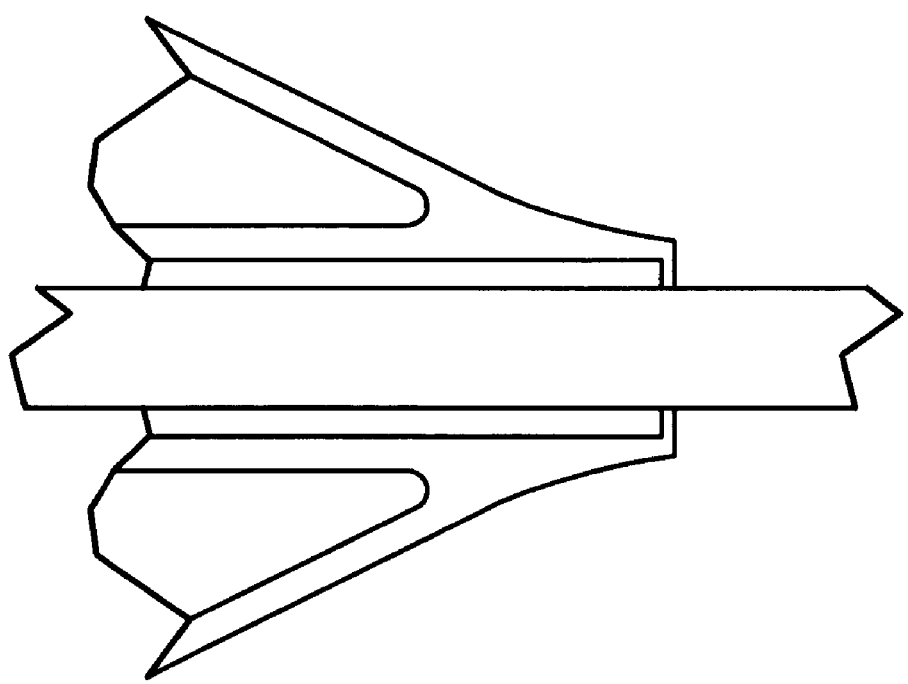
Figure 8:
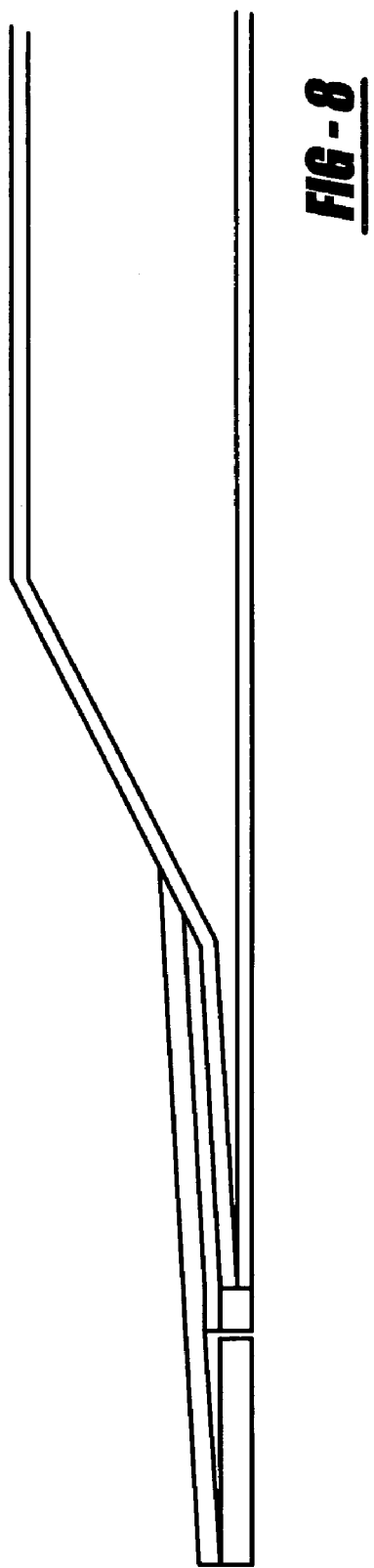
Figure 9:
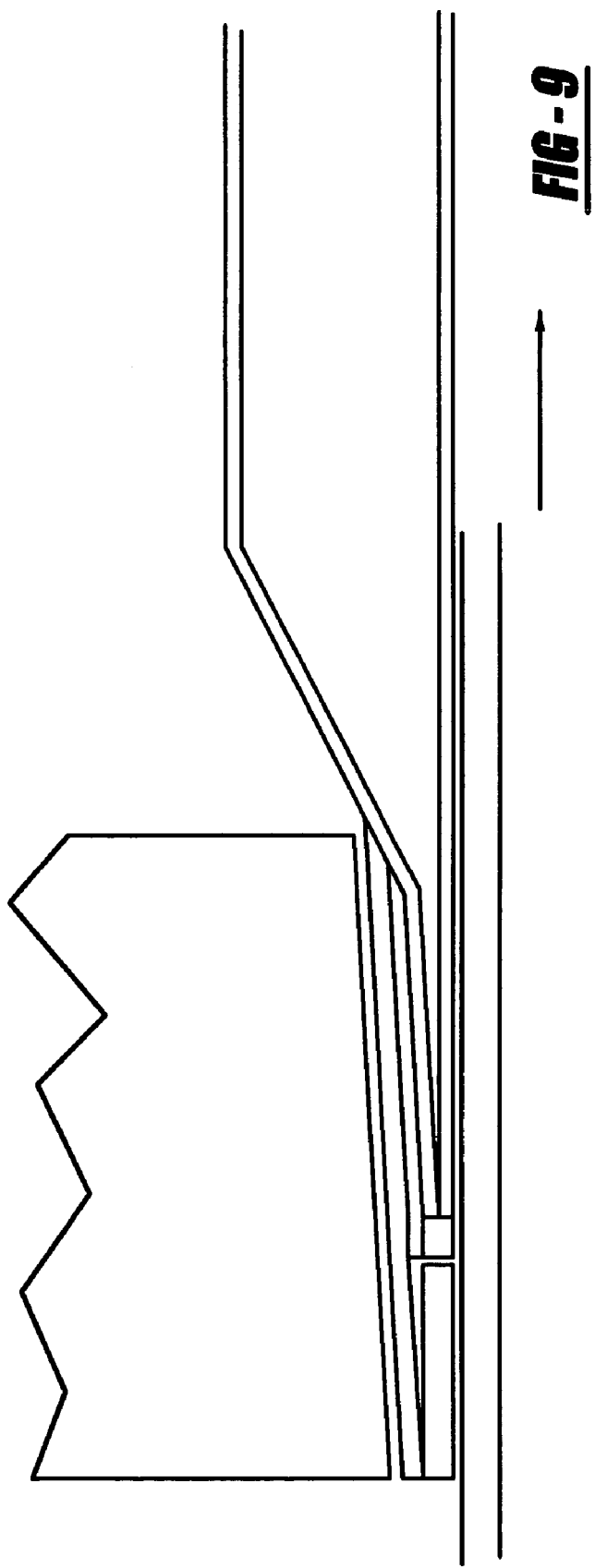
Figure 10:
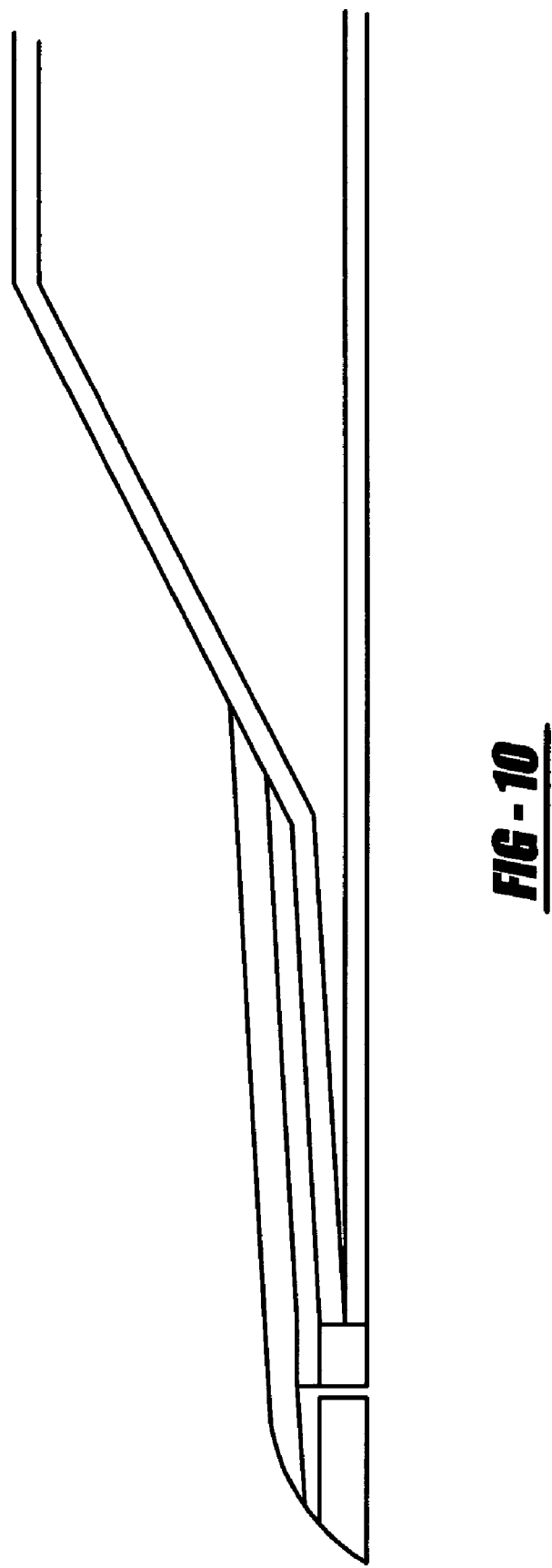
Figure 11:
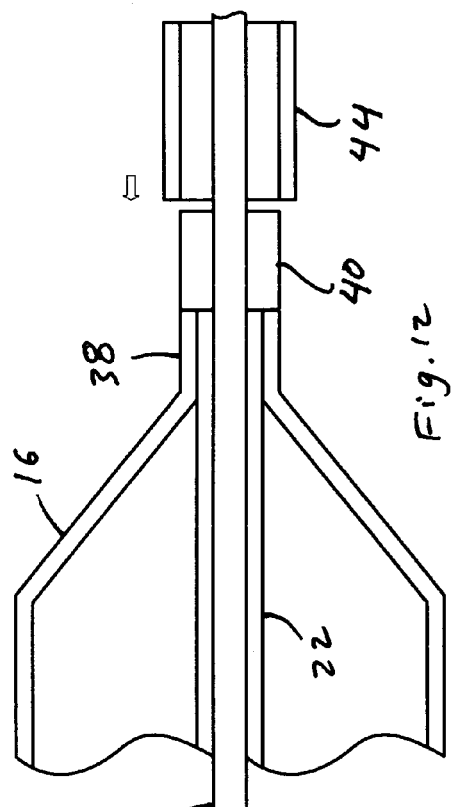
Figure 12:
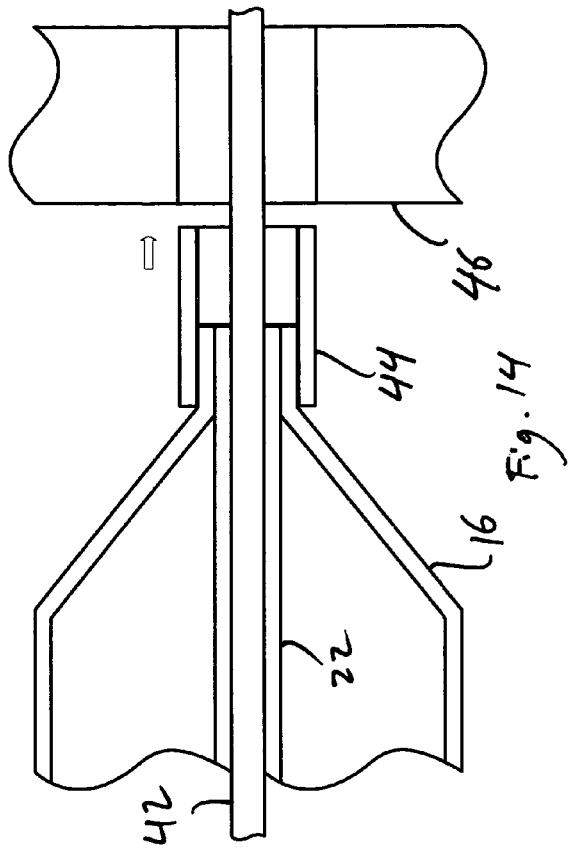
Figure 13:
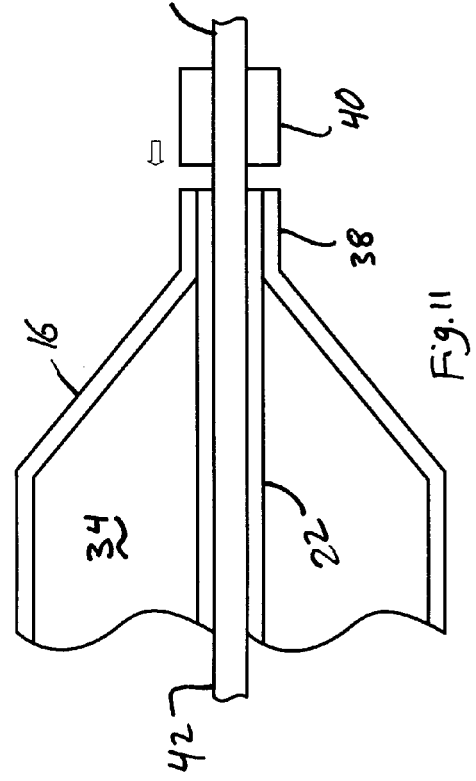
Figure 14:
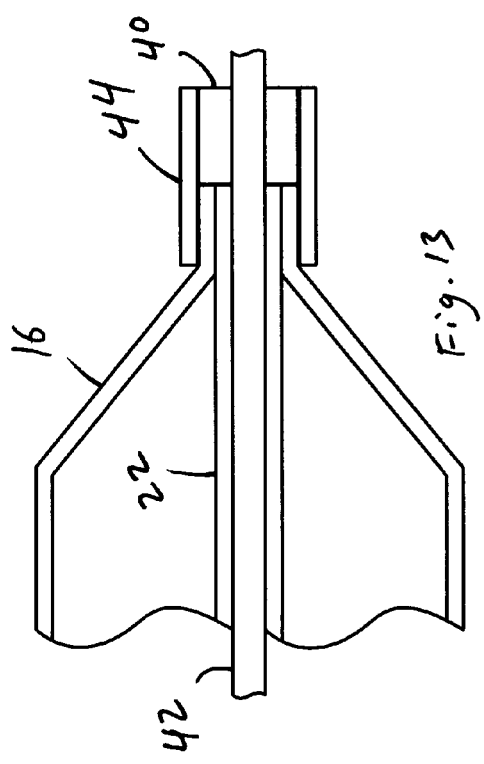
Figure 15:
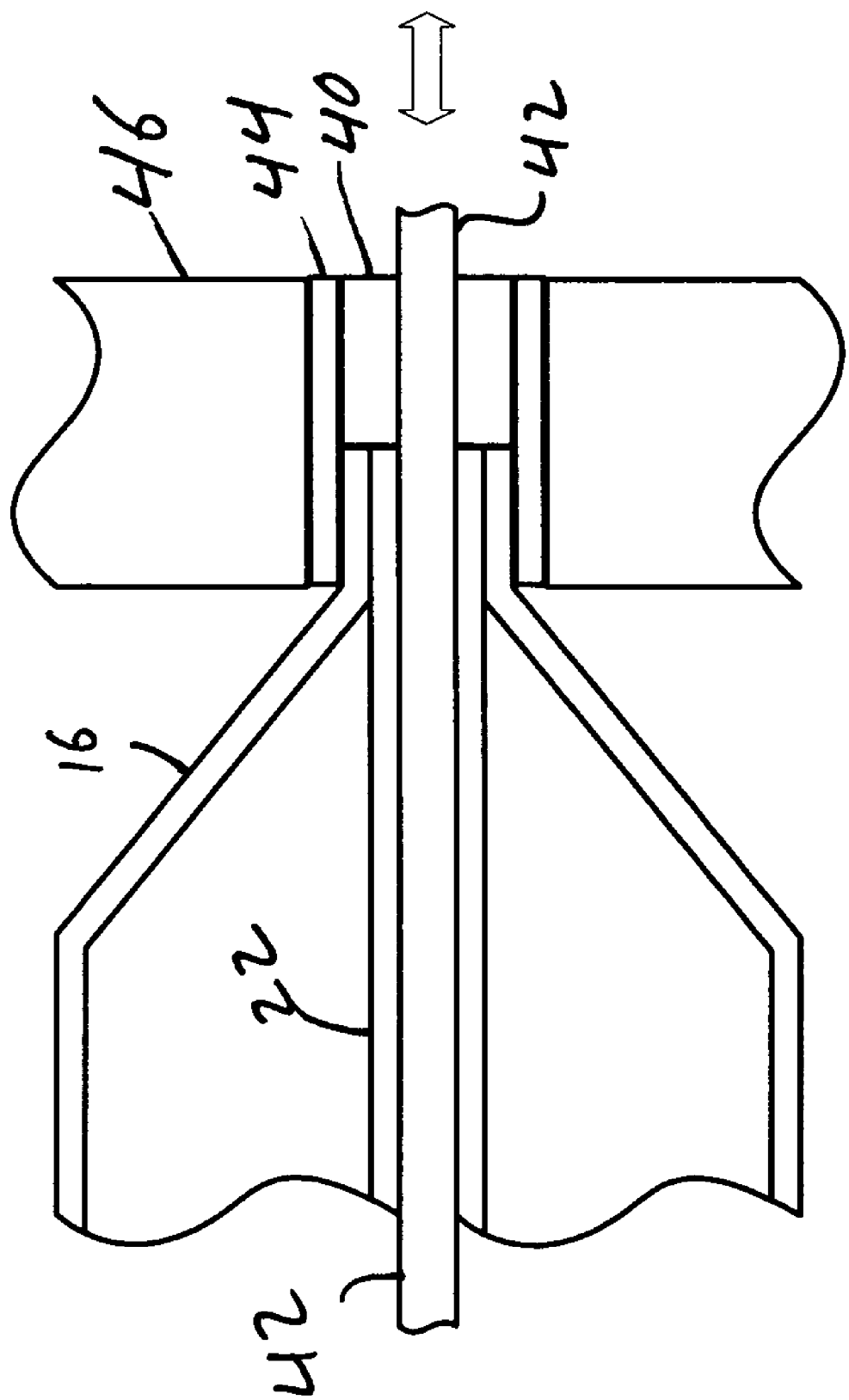

The following description of the preferred embodiments of the present invention is merely illustrative in nature, and as such it does not limit in any way the present invention, its application, or uses. Numerous modifications may be made by those skilled in the art without departing from the true spirit and scope of the invention.

Referring to the drawings, balloon catheters and methods of making them are depicted, with one of the examples of a balloon catheter being shown generally at 10. The illustrated balloon catheter of course depicts only one of many different balloon catheter designs within the scope of the present invention.

The drawings show an improved tip design and methods of the present invention, and includes a proximal hub 12, a flexible catheter shaft 14, and a balloon 16. The proximal hub 12 may provide an operating handle for a physician, as well as define a proximal guidewire port 18 and an inflation port 20.

At least a distal portion of the catheter shaft 14 may have a coaxial arrangement, including a tubular inner body 22 at least partially surrounded by a tubular outer body 24. The inner body 22 defines a guidewire lumen 26, extending from a distal guidewire port 28 defined at the distal tip of the catheter 10 to the proximal guidewire port 18. Guidewire lumen 26 can slidingly accept a guidewire 30. An inflation lumen 32 is defined by an annular space between the inner body 22 and outer body 24, extending from the proximal inflation port 20 to the balloon interior 34.

The balloon 16 may have a central cylindrical working portion, proximal and distal tapering portions, and proximal and distal legs 36 and 38. The balloon proximal leg 36 is affixed to a distal end of the outer body 24 by any suitable method, including heat-sealing or adhesives. Likewise, the balloon distal leg 38 is affixed to the inner body 22 near its distal end.

The positions of the proximal and distal ends of the balloon cylindrical working portion may be indicated under x-ray video or fluoroscopy by a pair of proximal and distal radiopaque marker bands affixed to the inner body 22.

The present invention provides a novel improved tip design having an optimized bundle of performance characteristics, including pull strength, column strength, a relatively smooth flexibility curve along the length of the catheter, and optimal distal tip flexibility. Additional features include minimum deflated outer profile, maximum guidewire lumen inner diameter, and hoop strength of the tubular inner body.

Accordingly, the illustrated example of the present balloon catheter preferably has a tubular distal tip member 40, which is placed in contact with a distally facing surface defined by the tubular inner body 22. The position or zone of contact may be called the contact location. If desired, distal leg 38 of balloon 16 may extend to the same location as distal end of inner body 22, as shown in the drawings, perhaps by cutting both inner body 22 and distal leg 38 after sealing them together. Alternately, tip member 40 may be affixed only to the inner body, with the distal leg of the balloon ending proximal of the inner body distal end.

At some point in the assembly process, a mandrel 42 is inserted within passages or lumens defined by the inner body 22 and the tip member 40, respectively. Inner body may be initially extruded onto mandrel 42, or a mandrel 42 may be later inserted.

After tip member 40 is in contact with inner body 22, a shrink tube 44 is placed around the contact location, and the resulting assembly is inserted within a heating die 46. The die 46 is heated, causing shrink tube 44 to be heated and tend to shrink radially inward, imparting a compressive force on tip member 40, balloon distal leg 38 and inner body 22. The heating should be sufficient to cause partial melting of tip member 40, balloon distal leg 38 and inner body 22.

While the heating takes place, the mandrel 42 is moved, tending to enhance interaction or even physical mixing of the polymer materials of tip member 40, balloon distal leg 38 and inner body 22. This interaction may be referred to as "blending" of the component materials. Of course, this use of the term "blending" is different from what is called a "polymer blend," which instead refers to mixing on a molecular level.

Movement of the mandrel 42 may be along the longitudinal axis, either in the distal direction or in the proximal direction, or the mandrel may be moved in both proximal and distal directions. Also, the mandrel may be rotated about the longitudinal axis.

Movement of the mandrel during heat and compressive pressure may be selected to cause the resulting blended tip to taper in the distal direction. If a steeper taper is desired for the tip, the interior of the heating die may be explicitly tapered. Other shapes for the heating die may also be selected.

The resulting tip provides a heat seal that is strong and flexible, and provides transitions in size and flexibility that may be tailored for desired characteristics.

The balloon catheter shown in the drawings has what is referred to as an over-the-wire configuration, in which the guidewire lumen extends throughout the length of the catheter to the proximal hub. Of course, the present invention may be used in a balloon catheter having a rapid-exchange configuration, in which the guidewire lumen extends from a distal guidewire port to a proximal port located at some intermediate position between the balloon and the proximal hub.

Various different materials may be used for the various components of a balloon catheter according to the present invention. Most of the balloon catheter components should preferably be made of materials having acceptable properties including biocompatibility, pull strength, longitudinal or column strength, and bending flexibility. Some of the materials may include various plastics, referred to as polymers, including nylon, polyethylenes including high density polyethylene (HDPE), polyurethanes, polyether block amide (PEBA) or PET. Also, any of the catheter components, including the inner body, may be made of a coextrusion of different polymers.

The shrink tube may be made of any suitable heat shrink material, including fluorinated polyethylene-propylene (FEP) or PTFE.

For example, the mandrel may be made of metal such as stainless steel. Various radiopaque materials are available for the markers, including gold, iridium and platinum.

The present invention may of course be made with any suitable selection of dimensions and sizes.

Other techniques for catheter manufacturing that are generally known in the art may be used in conjunction with the novel methods of the present invention, including extrusion and coextrusion, coating, adhesives, and molding. The scope of the present invention encompasses the full extent of the claims, regardless of specific materials, numbers or other details present in this description of the preferred embodiments.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A method of making a tip of a balloon catheter for performing a therapeutic procedure on a patient, comprising the steps of:
   a) providing a flexible catheter shaft having proximal and distal ends, at least a distal portion of the catheter shaft having a tubular body defining a lumen and a distal end with a distally facing surface; and providing an angioplasty balloon having a central inflatable portion and a pair of cylindrical proximal and distal legs;
   b) affixing the distal balloon leg to the tubular body at or near its distal end;
   c) providing a tubular tip member defining a lumen; and placing the tip member in contact with the distally facing surface of the tubular body, thereby defining a contact location;
   d) placing a shrink tube of heat-shrink material around the contact location; and inserting a wire mandrel through the lumens of the tubular body and tip member;
   e) heating the shrink tube sufficiently to cause the shrink tube to apply a radially compressive force to the tubular body and tip member, and to cause partial melting of the tubular body and the tip member; and
   f) while the shrink tube is at an elevated temperature, moving the wire mandrel longitudinally in the proximal and/or distal direction, such that portions of the tubular body and tip member blend together and seal the tip member to the tubular body.

2. The method of claim 1, wherein the balloon distal leg has a distal end located at or near the distal end of the tubular body, and wherein the tip member contacts and is sealed to both the tubular body and the balloon distal leg.

3. The method of claim 1, further comprising the following steps during or after said step d):
   providing a heating die having an inner surface;
   placing the tubular body, tip member and shrink tube within the heating die; and inserting a wire mandrel through the lumens of the tubular body and tip member.

4. The method of claim 3, wherein the heating die inner surface has a shape that tapers from a larger proximal size to a smaller distal size, such that the resulting balloon catheter tip has a tapering shape.

5. A method of making a tip of a balloon catheter for performing a therapeutic procedure on a patient, comprising the steps of:
   a) providing a flexible catheter shaft having proximal and distal ends, at least a distal portion of the catheter shaft having a tubular body defining a lumen and a distal end with a distally facing surface; and providing an angioplasty balloon having a central inflatable portion and a pair of cylindrical proximal and distal legs;
   b) affixing the distal balloon leg to the tubular body at or near its distal end;
   c) providing a tubular tip member defining a lumen; and placing the tip member in contact with the distally facing surface of the tubular body;
   d) providing a heating die;
   e) placing the tubular body and tip member within the heating die; and inserting a wire mandrel through the lumens of the tubular body and tip member;
   f) heating the die sufficiently to cause the partial melting of the tubular body and the tip member; and
   g) while the die is at an elevated temperature, moving the wire mandrel longitudinally in the proximal and/or distal direction, such that portions of the tubular body and tip member blend together and seal the tip member to the tubular body.

6. The method of claim 5, wherein the balloon distal leg has a distal end located at or near the distal end of the tubular body, and wherein the tip member contacts and is sealed to both the tubular body and the balloon distal leg.

7. The method of claim 5, wherein the heating die defines an inner surface with a shape that tapers from a larger proximal size to a smaller distal size, such that the resulting balloon catheter tip has a tapering shape.

* * * * *